United States Patent [19]

Saville

[11] Patent Number: 4,613,738

[45] Date of Patent: Sep. 23, 1986

[54] MICROWAVE HEATING DIGESTION VESSEL

[75] Inventor: Russell H. Saville, Minnetonka, Minn.

[73] Assignee: Savillex, Minnetonka, Minn.

[21] Appl. No.: 702,639

[22] Filed: Feb. 19, 1985

[51] Int. Cl.⁴ ............................................. H05B 6/80
[52] U.S. Cl. ...................... 219/10.55 R; 219/10.55 E; 220/316; 215/312; 215/315
[58] Field of Search ................ 219/10.55 R, 10.55 E, 219/431, 440; 220/366, 367, 361, 362, 316; 215/312, 311, 315; 99/369, DIG. 14; 426/241, 243, 403

[56] References Cited

U.S. PATENT DOCUMENTS

| | | | |
|---|---|---|---|
| 2,226,593 | 12/1940 | Stroupe et al. | 220/316 |
| 2,826,218 | 3/1958 | Barlow et al. | 215/312 X |
| 4,254,319 | 3/1981 | Beh et al. | 219/10.55 E X |
| 4,343,325 | 8/1982 | Fallon | 220/316 X |
| 4,395,940 | 8/1983 | Child et al. | 215/312 X |
| 4,406,861 | 9/1983 | Beauvais et al. | 219/10.55 R X |
| 4,490,597 | 12/1984 | Mengel | 219/10.55 E |

Primary Examiner—Philip H. Leung
Attorney, Agent, or Firm—Hugh D. Jaeger

[57] ABSTRACT

Microwave digestion vessel of Teflon PFA material including a Teflon PFA vessel with a threaded top and a Teflon PFA cap with internal threads for engaging the vessel threads. A valve assembly extends upwardly from a center portion of the cap and includes a valve seat, a valve ball internal thereto, a Teflon spring uniquely configured and a valve cap holding the spring and ball into the ball seat of the valve seat. An exhaust hole is provided out one side of the valve cap. The vessel includes a flange for encompassing a lower portion of the cap for pressure expansion protection. A ring with an adjoining flange is also provided for the cap to provide for pressure expansion protection.

9 Claims, 6 Drawing Figures

MICROWAVE HEATING DIGESTION VESSEL

BACKGROUND OF THE INVENTION

1. Field of the Invention

The present invention pertains to a digestion vessel, and more particularly pertains to a microwave digestion vessel for use in a microwave oven with a valve assembly for venting high pressure, the valve including the use of a Teflon spring acting against a Teflon ball.

2. Description of the Prior Art

Before the advent of microwave heating and microwave ovens, considerable time was required to dissolve samples for chemical analysis. This was especially so for elemental trace analysis, such as in the oil industry, the mining industry, and other related areas, including medical laboratories. Digestions were performed in open vessels on hot plates, or other heating devices, resulting in long and extended digestion times, in addition to the exposure of personnel to caustic and harmful exhaust fumes from boiling acids or other digestion subjects.

With the advent of microwave heating and microwave ovens, elemental trace analysis became ever more so common, especially in utilizing microwave digestion vessels in element trace analysis and the chemical procedures. The prior art problem with the using of digestion vessels was that there was a certain amount of guess work required in the microwave heating techniques, especially pertaining to temperature, pressure, and time for a digestion procedure. During microwave heating, it was possible, at elevated temperatures, to cause digestion vessels to expand considerably beyond normal size.

With the advent of Teflon PFA molded vessels, the Teflon PFA material provided a microwave digestion vessel which would function at elevated pressures and temperatures over time. Irrespective, there was still the necessity in the art for providing for the venting of high pressures and collection of vapors or gases in a slow controlled manner during microwave digestions.

Early attempts provided digestion vessels with valving assemblies with springs of ferrous or non ferrous alloys in a valving arrangement, but this proved to be difficult as such a metallic assembly in a microwave oven cavity may cause arcing between adjacent metallic members, and required special shielding and time consuming periodic cleaning off of surface oxidation for proper non impeded spring operation. These springs would also react with digestion vapors and gases offering potential contamination of the digestion container and contents thereof.

The present invention overcomes the disadvantages of the prior art by providing a microwave digestion vessel including a valve assembly, utilizing a Teflon ball and Teflon non-corrosive, non-contaminating spring, and including a pressure release hole out the side of the valve for exhausting pressure on actuation of the valve spring in a slow controlled manner.

SUMMARY OF THE INVENTION

The general purpose of the present invention is a microwave digestion vessel for use in digestion procedures in a microwave oven. Particularly, the Teflon PFA digestion vessel includes a Teflon valve assembly, the Teflon valve assembly including a unique Teflon spring acting in conjunction with a Teflon ball for venting of high pressures in a slow controlled manner.

According to one embodiment of the present invention, there is provided a microwave digestion vessel including a Teflon PFA vessel with a threaded top, a Teflon PFA cap with mating threads to the vessel, the cap including a valve assembly having a valve seat, the valve seat including a ball seat and a Teflon noncorrosive, non-contaminating valve spring acting between a valve cap, which threads onto the valve seat, and a Teflon ball. An exhaust hole is provided in one side of the valve seat for exhausting gasses under pressure. The Teflon valve spring includes a section of spring with two open cylinders on each end. A plurality of spacing nipples extend outwardly from the sides of the cylinders, as well as the sections of spring, for spacing the spring within the round interior section leading to the valve seat. A small clearance is provided adjacent to the ball at the valve seat for slow controlled venting of pressure.

One significant aspect and feature of the present invention is a Teflon PFA microwave digestion vessel with a Teflon venting valve including a Teflon spring for relieving high pressures during digestion procedures.

Another significant aspect and features of the present invention is a Teflon PFA microwave digestion vessel utilizing a Teflon valve spring in a Teflon valve assembly. The Teflon valve spring is transparent to microwave energy, and does not heat up during the microwave heating process in the microwave oven, as well as being non-contaminating and non-corrosive.

Having thus described embodiments of the present invention, it is a principal object hereof to provide a microwave digestion vessel with a pressure relieving valve for use in a microwave oven during digestion procedures for bleeding off pressure and fumes in a controlled manner.

One object of the present invention is to provide a microwave digestion vessel which includes an entire Teflon valve assembly for relieving high pressure build up in the vessel during digestion procedures in a microwave oven utilizing a slow controlled venting procedure based on the design of the valve.

Another object of the present invention is to provide a microwave digestion vessel which includes a noncorrosive Teflon spring which will not corrode and impede valve operation.

Another object of the present invention is to provide a microwave digestion vessel which includes a noncorrosive Teflon spring which will not contaminate the gases or vapors from the vessel nor the contents thereof.

DESCRIPTION OF THE PREFERRED EMBODIMENTS

Figure 1:
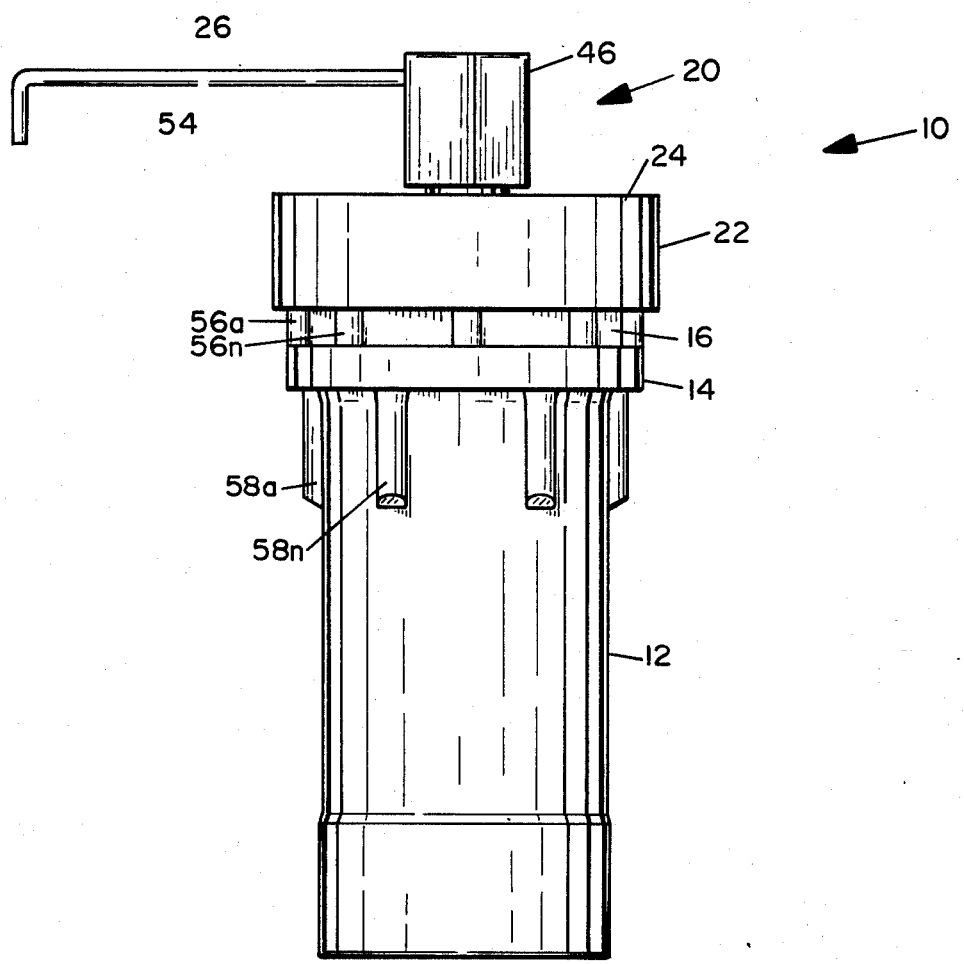
FIG. 1 illustrates a side view of a microwave digestion vessel including a pressure relieving valve assembly.
Figure 2:
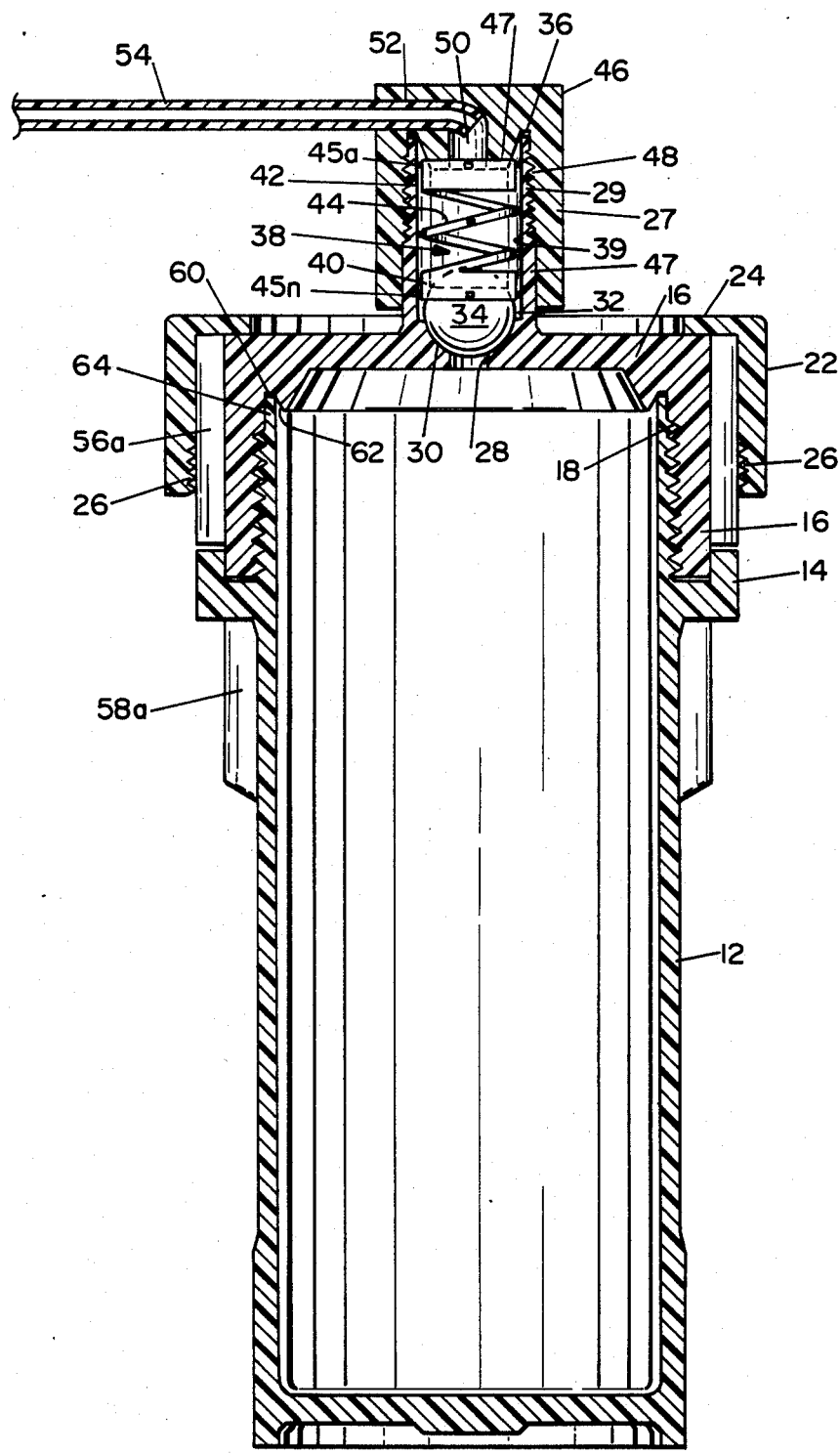
FIG. 2 illustrates a cross section of the vessel and valve assembly.

FIG. 1 illustrates a side view of a microwave digestion vessel 10 including a Teflon PFA vessel 12 with a threaded top 13, as illustrated in FIG. 2, and a molded flange 14 for encompassing a lower portion of a Teflon PFA cap 16 with internal threads 18, as illustrated in FIG. 2. A valve body 20 extends upwardly from the top of the cap 16, and is described in detail in FIG. 2. A venting tube 54 extends outwardly from the valve cap 46 as later described. A retaining ring 22 with a top leading edge 24 surrounds an upper portion of the cap 16 and includes internal threads 26 as illustrated in FIG. 2. The ring 22 provides that cap 16 cannot expand away from the vessel 12 during microwave digestion procedures at elevated temperatures. Threads 26 are self threading providing for loose screwing of the ring 22 on and off of the cap 16 as required.

FIG. 2 illustrates a cross-sectional view of FIG. 1 where all numerals correspond to those elements previously described. Particularly, the valve body 20 includes a central hole 28, a ball seat 30, and narrow aperture clearance 32 upwardly extending on an interior section of an upwardly extending valve body wall 27. The ball seat is positioned about a lower portion of a ball 34 in the top wall of the cap 16. Top 36 of the valve body 20 is planar providing for a positive stop. The Teflon ball 34 engages against the ball seat 30. A Teflon spiral spring 38 engages within the internal cylindrical wall section 39 of the valve body 20. The Teflon spring 38 includes two open cylindrical members 40 and 42 connected by a section of spiral spring 44. A plurality of spacing nipples 45a–45n extend outwardly from the members 40–44. Each cylindrical member 40 and 42 includes a 45° chamber or a rounded chamber, and a flat surface as later described in FIG. 3. A valve cap 46 includes interior threads 48 which engage with threads 29 of the valve body 47, providing for an integral fit. A top underside surface 47 of valve cap 46 is also planar providing for a positive stop and mating with the planar surface 36 of valve body 20. A hole 50 extends upwardly to a side hole 52 for venting of pressures out the side of the valve cap 46. A relief tube 54 can be pressed into the side hole 50 for relieving and draining residual fluids into a second container as later described. The Teflon spring can be glass filled, a composite, or the like, for maintaining a proper flexible spring coefficient. The vessel bottom, vessel cap, and valve seat and cap, as well as the ball and spring, can also be made out of other materials than Teflon PFA. The spring section can also assume any other like geometrical configuration such as a "Z" shape, etc., rather than the spiral shape as illustrated. The ring 22 can be of a polymer, a composite, or other like material. The flange 14 is of an annular right angle shape so that the lower portion of the cap 16 screws and extends down into the area created by the encompassing annular flange so that the cap 16 will not expand off of the threaded vessel top 13 during digestion processes which create height pressures. The top of the vessel 12 includes a flat planar lip edge 60 with annular exterior edge 64. The interior of the cap 12 includes an angled annular interior wedge edge 62. As the cap 16 is screwed on tightly, angled wedge edge 62 exerts outward force upon lip edge 60 and forces it and the annular exterior edge 64 outwardly effecting a secure pressurized seal between edge 64 and the adjacent interior cap surface, as well as between wedge edge 62 and portions of lip edge 60. It is illustrated that the two planar surfaces 36 and 47 of valve body 20 and valve cap 46, respectively, mate flush with each other's surfaces.

Figure 3:
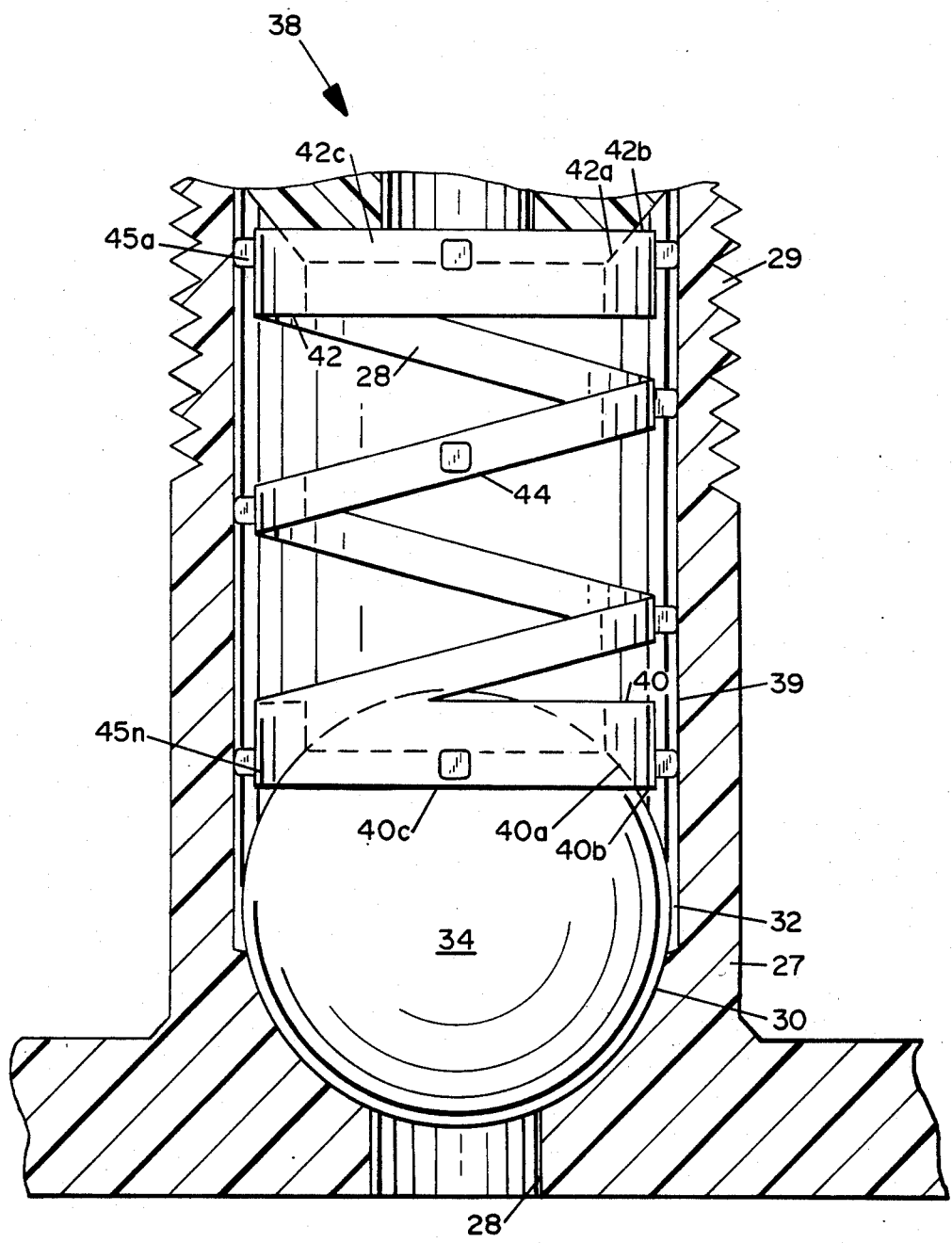
FIG. 3 illustrates an enlarged view of a portion of the valve assembly.

FIG. 3 illustrates an enlarged view of the valve body 27, ball 34, and the spring 38. Each open cylindrical member 40 and 42 includes a 45° or conforming chamber 40a and 42a and a flat surface 40b and 42b. Hollow portions 40c and 42c through members 40 and 42 are provided for venting of gases, vapors, etc. The spring 38 is interchangeable in either direction for ease of installation. The spring includes a plurality of spacing nipples 45a–45n for spacing elements 40–44 from the side wall 39. The spring can be of one to ten turns, while two turns are illustrated by way of example and for purposes of illustration only. The transition from the ball seat 30 to the clearance of each side of the 34 in hole 28 is in the range of 20/1000 inch for controlling pressure release, although any other suitable dimension can be utilized as parameters would require.

Figure 4:
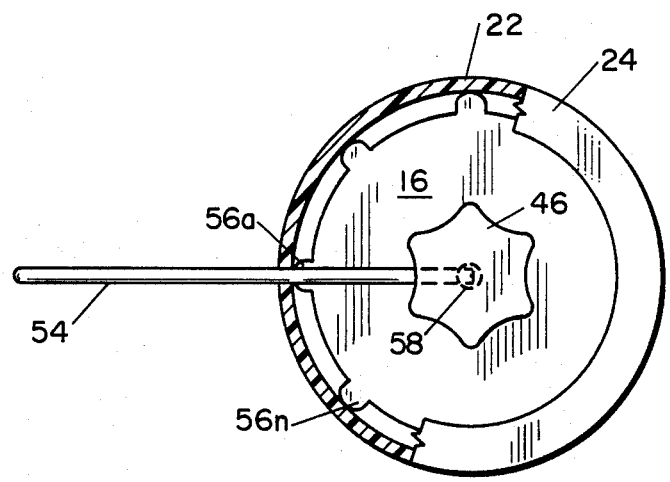
FIG. 4 illustrates a partial cutaway top view of the vessel.

FIG. 4 illustrates a top view in partial cross section of the present invention where all numerals correspond to those elements previously described. In this view, as well as the bottom view of FIG. 5, a plurality of downwardly extending lugs 56a–56n are provided for the cap 16, and a plurality of like downwardly extending lugs 58a–58n are provided for the vessel 12. These ribs provide point contact gripping point for a lug tool to separate the top and bottom of the vessel. The lower lugs 58a–58n are molded into the lower edge of flange 14 for structural integrity and stability.

MODE OF OPERATION

Figure 6:
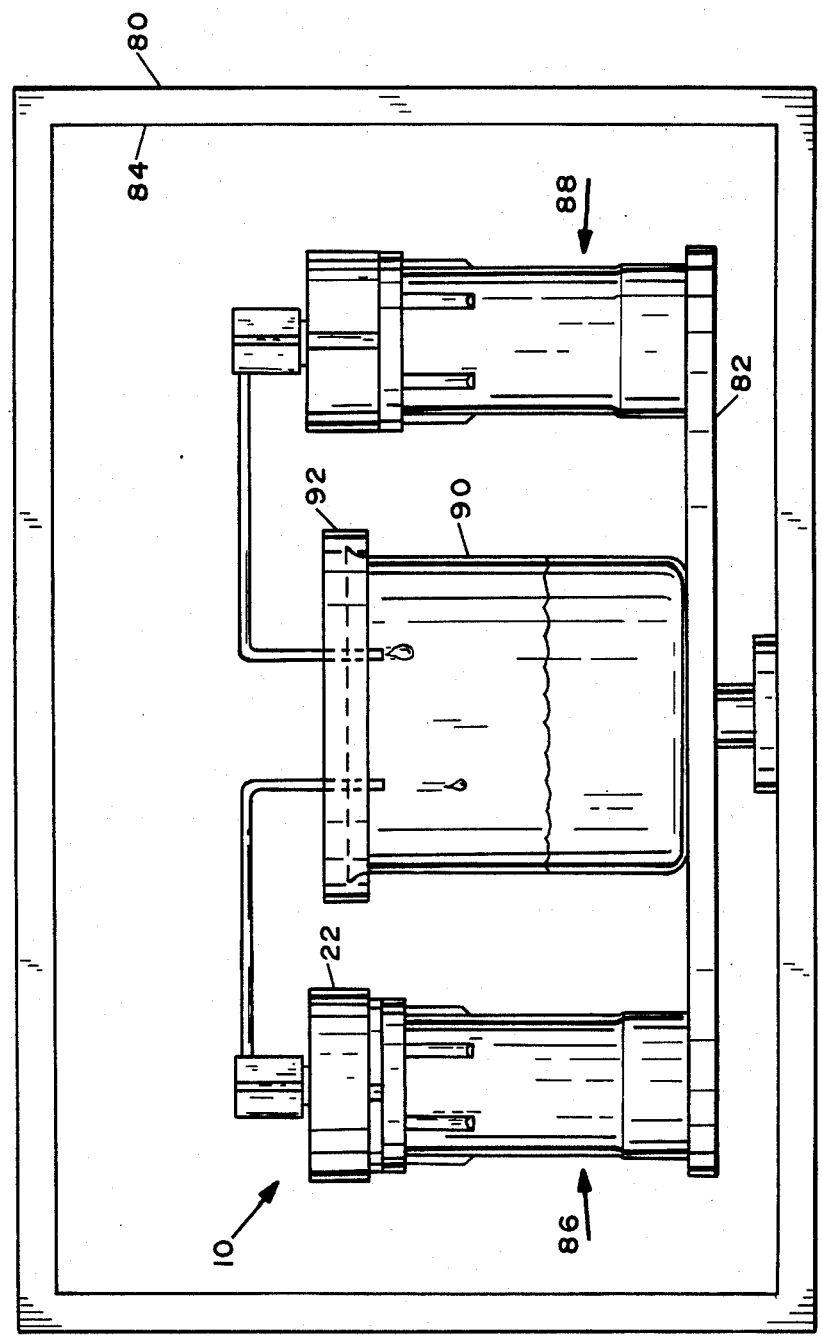
FIG. 6 illustrates vessels used in a microwave oven during a microwave digestion procedure.

FIG. 6 illustrates the mode of operation of the present invention, illustrating a microwave oven 80, and a turntable 82 in the microwave oven cavity 84 for supporting a plurality of digestion vessels 10 about the perimeter of the turntable 82. Two digestion vessels 86 and 88 are shown by way of example and for purposes of illustration only. A container 90 positions on the axis of the turntable. The microwave digestion vessles include relief tubes from the hole of each valve assembly coupled into the container for discharge of any residual pressure, vapors, or liquids, etc. The container 90 can include a cap 92. The container and cap can be made of Teflon, glass, or any other material transparent to microwave energy.

Figure 5:
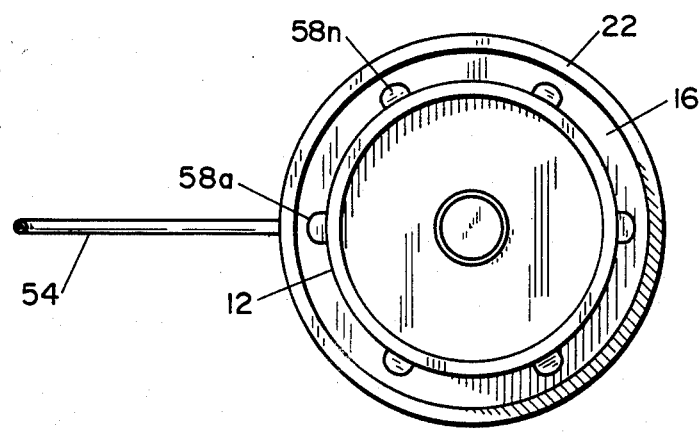
FIG. 5 illustrates a bottom view of the vessel.

In operation, and referring particularly to FIGS. 2 and 3, when the pressure becomes high enough to overcome the spring coefficient, the ball 34 is unseated off the ball seat 30, and pressure flows around the circumference of the ball at clearance 32, up and around the open cylinders 40 and 42 including the spring section 44 as spaced by the spacing nipples 40a–40n. Gas exhausts through the top surface of the cylinder 42 and out through the vent holes 50 and 52 and tube 54. The tube 54 channels the gas and vapors into the container 90 as illustrated in FIG. 5 or the unit can be operated with a short tube exhausting to open air inside the oven or with no tube. Each vessel can be used without the retaining ring 22 as so desired. The bottle, cap, and ring will be made of materials transparent to microwave energy. The material, while indicated as a fluoropolymer, such as Teflon PFA, can include a glass fiber filler, rag content, or a composite material. The ring can also be made of a polymer as required. The vessels can be used with or without the ring as illustrated in FIG. 5 where one vessel is illustrated with the ring 22 and the other vessel is without the ring.

Various modifications can be made to the present invention. The hole 28 can be varied in diameter which would vary the release pressure. Likewise, the spring compression is adjustable by the number of turns, diameter of the cross-section, etc.

I claim:

1. A microwave heating digestion vessel for use in a microwave oven during a microwave heating digestion of a material comprising:
   a. molded threaded vessel and mating molded threaded lid for covering said vessel, said vessel and said lid being transparent to microwave energy;
   b. valve assembly affixed to the top of said lid, said valve assembly including a ball seat with a vent opening disposed in said lid, a hollow cylindrical stem including a threaded outer portion, said cylindrical stem supporting a spring assembly therein and affixed to said lid about said ball seat, a flat positive planar stop surface at the top of said cylindrical stem and a valve cap including a threaded inner portion and an interior flat planar stop surface, said threaded valve cap covering said cylindrical stem and retaining said spring assembly, said spring assembly acting on top of and against a ball mating in said ball seat, wherein said spring assembly comprising two opposing open cylindrical sections, a section of a spiral spring between said cylindrical sections, and a plurality of spacing nipples extending outwardly from said open cylindrical sections and said spring section providing for passage of pressure and vapors about said cylindrical and spring sections; and
   c. venting hole means disposed in said valve cap for exhausting pressure, vapors and liquid from said vessel.

2. The microwave heating digestion vessel of claim 1 wherein each of said open cylindrical sections includes a chambered interior to engage with said ball and a flat planar surface for engaging with an underside surface of said valve cap.

3. The microwave heating digestion vessel of claim 1 wherein said molded threaded vessel and lid are made of fluorocarbons.

4. The microwave heating digestion vessel of claim 1 including an encompassing cylindrical flange extending upwardly from a mid-portion of said vessel and encompassing said lower edge of said lid.

5. The microwave heating digestion vessel of claim 1 including a ring assembly with an encompassing top leading edge and a ring of diameter to loosely engage down over said lid to a point where said lid threads onto said vessel and said top leading edge supporting said ring assembly about said lid.

6. The microwave heating digestion vessel of claim 1 wherein said spring assembly is made of flurocarbons.

7. The microwave heating digestion vessel of claim 1 wherein said spring assembly is of a composite material.

8. The microwave heating digestion vessel of claim 1 wherein said spring section comprising 1-10 turns.

9. A microwave heating digestion vessel for use in a microwave oven during a microwave heating digestion procedure comprising:
   a. molded threaded vessel and mating molded threaded lid for covering said vessel, said vessel and said cap being transparent to microwave energy;
   b. cylindrical flange extending upwardly from a mid-portion of said vessel for encompassing a lower edge of said lid;
   c. valve assembly affixed to the top of said lid, said valve assembly including a ball seat with a vent opening disposed in said lid, a tubular cylindrical stem supporting a spring assembly and affixed to said lid about said ball seat, a flat positive planar stop surface at the top of said cylindrical stem, a threaded outer portion about said cylindrical stem, and a valve cap including a threaded inner portion and an interior flat planar stop surface, said threaded valve cap retaining said spring assembly, said spring assembly acting on top of and against a ball mating in said ball seat, wherein said spring assembly comprising two opposing open cylindrical sections, a section of a spiral spring between said cylindrical sections, and a plurality of spacing nipples extending outwardly from said open cylindrical sections and said spring sections providing for passage of pressure and vapors about said cylindrical and spring sections;
   d. venting hole means in said valve cap for exhausting pressure, vapors and liquids from said vessel; and,
   e. ring assembly means encompassing and engaging about said lid.

* * * * *